United States Patent
Nycz et al.

(10) Patent No.: US 7,118,029 B2
(45) Date of Patent: Oct. 10, 2006

(54) SMART INSTRUMENT TRAY RFID READER

(75) Inventors: Jeffrey H. Nycz, Collierville, TN (US); Steven M. Tethrake, North Webster, IN (US); Mark Pelo, Macy, IN (US)

(73) Assignee: SDGI Holdings, Inc., Wilmington, DE (US)

( * ) Notice: Subject to any disclaimer, the term of this patent is extended or adjusted under 35 U.S.C. 154(b) by 52 days.

(21) Appl. No.: 10/927,475

(22) Filed: Aug. 27, 2004

(65) Prior Publication Data

US 2006/0043179 A1 Mar. 2, 2006

(51) Int. Cl.
*G06F 17/00* (2006.01)

(52) U.S. Cl. .................................................... 235/375

(58) Field of Classification Search ................ 702/184; 705/29; 340/10.2, 10.3; 235/375
See application file for complete search history.

(56) References Cited

U.S. PATENT DOCUMENTS

| | | | |
|---|---|---|---|
| 4,075,632 A | 2/1978 | Baldwin et al. | |
| 4,360,801 A | 11/1982 | Duhame | |
| 4,390,880 A | 6/1983 | Henoch | |
| 4,739,328 A | 4/1988 | Koelle et al. | |
| 5,030,807 A | 7/1991 | Landt et al. | |
| 5,950,632 A | 9/1999 | Reber et al. | |
| 6,223,137 B1* | 4/2001 | McCay et al. | 702/184 |
| 6,259,369 B1 | 7/2001 | Monico | |
| 6,366,206 B1* | 4/2002 | Ishikawa et al. | 340/573.1 |
| 6,650,227 B1* | 11/2003 | Bradin | 340/10.3 |
| 2002/0049650 A1* | 4/2002 | Reff | 705/29 |
| 2002/0143320 A1 | 10/2002 | Levin | |
| 2002/0188259 A1 | 12/2002 | Hickle et al. | |
| 2002/0196126 A1* | 12/2002 | Eisenberg et al. | 340/10.2 |
| 2003/0052788 A1 | 3/2003 | Chung | |
| 2003/0178488 A1 | 9/2003 | Southard | |
| 2004/0008123 A1 | 1/2004 | Carrender et al. | |

* cited by examiner

*Primary Examiner*—Thien M. Le
*Assistant Examiner*—Kirsty A. Haupt
(74) *Attorney, Agent, or Firm*—Hunton & Williams LLP

(57) ABSTRACT

A method and apparatus for automatically identifying the contents of an instrument tray by use of a radio-frequency tag (RFID) is disclosed. The method, apparatus, and system enable the instrument tray to receive an interrogation signal from a reader and to respond to the interrogation signal with a code comprised of its identifying information as well as its contents of radio frequency tagged instruments. Both the instrument tray and/or the reader may be coupled by a proximity electromagnetic field, an inductive coupling, or may be units of a wireless LAN system such as a wireless fidelity local area network. The interrogation signal interrogates the tray to ascertain its contents, and the tray in turn transmits a signal to the reader to inform the reader of its contents. The method, apparatus, and system can track, inspect, and verify inbound and outbound surgical instrument trays and kits, to assess, for example, the surgical instruments' and trays' duty life cycle usage.

28 Claims, 4 Drawing Sheets

SMART INSTRUMENT TRAY RFID READER

FIELD OF THE INVENTION

The invention generally relates to a method and apparatus for implementing radio frequency identification techniques, and more specifically, to a method and apparatus for tracking, inspecting and verifying inbound and outbound surgical instrument kits in order to assess the surgical instruments' duty life cycle usage.

DESCRIPTION OF RELATED ART

A variety of methods exist for tracking and providing information about items. For example, inventory items typically carry printed labels providing information such as serial numbers, price, weight, and size. Some labels include data carriers in the form of machine-readable symbols that can be selected from a variety of machine-readable symbologies, such as bar code or area code symbologies. The amount of information that the symbols can contain is limited by the space constraints of the label. Updating the information in these machine-readable symbols typically requires the printing of a new label to replace the old.

Data carriers such as memory devices provide an alternative method for tracking and providing information about items. Memory devices permit the linking of large amounts of data with an object or item. Memory devices typically include a memory and logic in the form of an integrated circuit ("IC") and a mechanism for transmitting data to and/or from the device. For example, a radio frequency identification ("RFID") tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are incorporated herein by reference in their entirety. RFID tags are generally formed on a substrate and can include, for example, analog RF circuits and digital logic and memory circuits. The RFID tags also can include a number of discrete components, such as capacitors, transistors, and diodes. The RF transmission of data can be accomplished with modulated back scatter as well as modulation of an active RF transmitter.

RFID tags can either be passive or active devices. Active devices are self-powered, by a battery for example. Passive devices do not contain a discrete power source, but derive their energy from an RF signal used to interrogate the RFID tag. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, the RFID tag can permit new or additional information to be stored in the RFID tag's memory, or can permit the RFID tag to manipulate data or perform some additional functions.

Another form of memory device is an optical tag. Optical tags are similar in many respects to RFID tags, but rely on an optical signal to transmit data to and/or from the tag. Additionally, touch memory devices are available as data carriers, (e.g., touch memory devices from Dallas Semiconductor of Dallas, Tex.). Touch memory devices also are similar to RF tags, but require physical contact with a probe to store and retrieve data.

Tracking and managing surgical instruments used by hospitals is important to the efficiency and safety of use of hand held medical or surgical instruments. Medical instruments typically are gathered after an operation or other procedure, including instruments in the form of sterilized sets, e.g., tray set-ups, for the patient's specific medical procedure. It is desirable to be able to identify an inventory of the medical instruments to facilitate repair and replacement of these instruments, should they become broken or worn. Any device attached to a medical device or surgical instrument must be capable of performing despite being attached to various metals, and must be able to withstand the rigors of sterilization.

Most of the existing methods employ color-coding techniques to identify different surgical instruments. Others optically mark each instrument, and later scan the instruments with a hand-held scanner that is connected to a data terminal to ascertain the history of that instrument. Such a method typically requires that the instrument be removed from the tray on arrival, and scanned by humans, a method that is costly, and time-consuming.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

There is a need to provide inventory systems for medical and surgical devices that is more efficient for reducing handling costs, automating the verification process of items such as surgical instruments, and to overcome the aforementioned interference problems.

Embodiments of the invention provide a method and apparatus for automatically and wirelessly inventorying surgical instruments and the like, by retrieving information from the instrument. The information preferably may include information indicative of the manufacturer, part number, serial number and manufacturing data, usage and maintenance history of each instrument, and the like. The inventive method and apparatus allow for lower handling costs of surgical instruments, increase the accuracy of the verification process of data pertaining to each instrument with a reduction of human contact, and provide for real-time data collection resulting in fast data acquisition that speeds up the inventory updating of such instruments.

Embodiments of the invention also are capable of circumventing some of the problems associated with manual removal and scanning of surgical instruments by implementing radio frequency tagging of each instrument, and creating a database on a wireless reader in order to wirelessly compare and ascertain the history of each tagged instrument as it arrives in a distribution center. One advantage of using RFID is that it does not require direct contact or line-of-sight scanning. An RFID system preferably includes three components: (i) an antenna; (ii) a transceiver (often the antenna and transceiver are combined into one reader); and (iii) a transponder (the RF tag) electronically programmed with certain unique information. The antenna emits radio frequency waves to activate the transponder (tag) in order to read or write data to it. In turn, the tag transmits data back to the antenna, and the data can be used to interface with a database to carry out a function such as inventory processing.

A feature of an embodiment of the invention provides a method and apparatus for automatically and wirelessly inventorying surgical instruments and the like. The method and apparatus preferably retrieves information from the medical device or surgical instrument, such information may be indicative of the manufacturer, part number, serial number, manufacturing data, usage, and maintenance history of each instrument. The method and apparatus allows for lower handling costs of surgical instruments, increases the accuracy of verification process of data pertaining to each instrument with a reduction of human contact, and provides real-time data collection resulting in fast data acquisition, which ultimately speeds up inventory updating of such instruments.

According to a feature of an embodiment of the invention, an instrument tray, (e.g., a "smart" instrument tray), including a plurality of medical and/or surgical instruments that optionally may be positioned in or on the tray, comprises one or more radio frequency identification tags (RFID Tags) that identify each instrument and the accompanying tray. It is preferred, though not required, that the tags identify each instrument in terms of manufacturer, part number, name, usage, and maintenance history. The method of the invention includes presenting the smart instrument tray, optionally including a plurality of instruments, into a wireless radio frequency field of a reader device that emits an RF signal, activating the one or more RFID tags, and enabling a response by the tags via a transceiver/antenna combination. The transceivers along with the antenna, collect data from the RFID tags and passes the data in a wireless fashion to the wireless reader to determine actions needed to be taken such as refurbishing, discarding or any other action deemed necessary of the instruments.

Another embodiment of the invention provides a method and apparatus for identifying and inventorying instruments used in surgical procedures. This embodiment provides a smart instrument tray that optionally contains a plurality of RFID tagged surgical or medical instruments, wherein the RFID tags contain data identifying the instruments and optionally the tray. In a preferred embodiment of the present invention, the RFID tags are interrogated by a combination of transceivers and antenna. In response to an interrogation signal, the RFID tags on the instruments respond by transmitting a signal back to the transceiver/antenna combination, whereby the signal may contain data such as an individual identification data. The data then are compared against a database containing information about the contents of each smart instrument tray, and when it is determined that an individual RFID tag belongs to the individual instrument tray, a signal is transmitted to a module on the exterior of the smart instrument tray to activate a light emitting diode (preferably a green light).

On the other hand, when data from the RFID tag does not match information in the database, a signal is transmitted to a module on the exterior of the smart instrument tray to activate a LED (preferably a red light) signifying that the instrument belongs to another instrument tray, thereby allowing for faster processing of inbound instrument trays that returned from the customers. This feature of the invention may be modified to include a sound generation signal as opposed to a LED signal. For example, if the instruments are properly positioned in the appropriate instrument tray, a single beep may sound, whereas if the instruments are not properly positioned, a longer sustained beep, or multiple beeps may sound.

Another embodiment of the present invention provides a method, apparatus, and system for identifying medical and surgical instruments in an instrument tray, wherein outbound instrument trays are packaged together in a warehouse, and wherein inbound instrument trays that arrive from customers are received and processed. A typical system of this embodiment includes, but is not limited to, an instrument tray, desk-top personal computer(s), lap-top computer(s), personal digital assistant(s) (such as Palm™ Tungsten™), and/or sub-notebook. Various combinations of these items may be included in the system, and not all items need be present. These items comprise a wireless fidelity (WIFI) local Area Network that implements a peer-to-peer network, thereby allowing all the wireless equipment in the warehouse to communicate with each other without the need for a gateway or an access point.

One aspect of this embodiment provides a method whereby: (i) a smart instrument tray, together with a plurality of RFID tagged medical or surgical instruments, arrives at a central distribution center; (ii) a hand-held Wi-Fi-capable personal digital assistant transmits an interrogation signal; (iii) in response to the interrogation signal, a transceiver/antenna combination that is incorporated into the plurality of tagged instruments, including the instrument tray, interrogates the RFID tagged items and receives a data signal back; (iv) the plurality of tagged instruments transfers the data to the hand-held personal digital assistant; and (v) the data are compared to information maintained in a local database pertaining to the history of each individual instrument and tray.

Other aspects and advantages of the invention will become apparent from the following detailed description, taken in conjunction with the accompanying drawings, illustrating by way of example the principles of the invention.

BRIEF DESCRIPTION OF THE DRAWINGS

Purposes and advantages of the present invention will be apparent to those of ordinary skill in the art from the following detailed description in conjunction with the appended drawings in which like reference characters are used to indicate like elements, and in which.

DETAILED DESCRIPTION OF THE PREFERRED EMBODIMENTS

The following description is intended to convey a thorough understanding of the invention by providing specific embodiments and details involving automating and adding value to medical and surgical instruments, and instrument kits. It is understood, however, that the invention is not limited to these specific embodiments and details, which are exemplary only. It further is understood that one possessing ordinary skill in the art, in light of known systems and methods, would appreciate the use of the invention for its intended purposes and benefits in any number of alternative embodiments, depending upon specific design and other needs.

Figure 1:
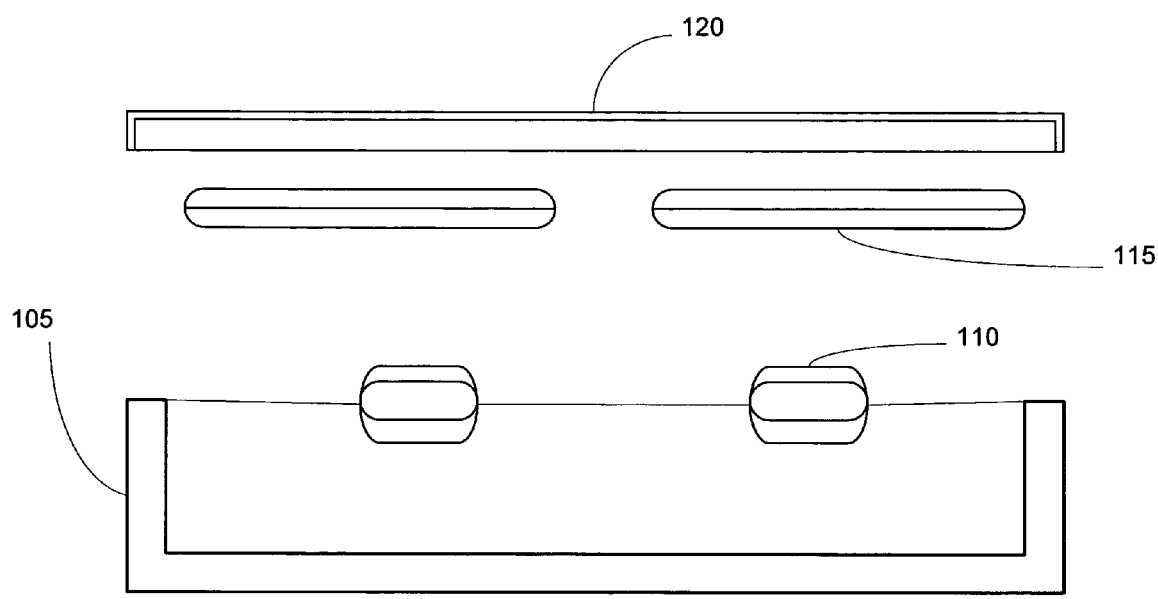
FIG. 1 is a schematic diagram of a smart instrument tray according to an embodiment of the invention.

Referring to FIG. 1, a smart instrument tray 105 is illustrated in accordance with one feature of an embodiment of the invention. The smart instrument tray 105 is part of a wireless communication system that includes one or more transceivers 110, one or more antenna 115, optionally a plurality of radio frequency tagged instruments placed in the tray (not shown), and optionally a lid 120 that keeps the contents as well as the transceivers and antenna in place. Typically, the one or more antenna 115, is attached to any part of the inside of the instrument tray 105, such as the inside of the lid, the inside bottom of the tray, or on any other internal stray portion. Typically, the medical or surgical instruments are radio frequency tagged with passive RFID tags to enable the identity of each instrument to be remotely and accurately inspected and verified. The RFID tags also enable determination of each instrument's history of usage, repair, and age. Any other data important or relevant to surgical instruments also may be encoded into the RFID tag, as will be appreciated by those skilled in the art. Because the RFID tags preferably are passive, an alternating current created by the received carrier signal supplies power to the tags.

Figure 2:
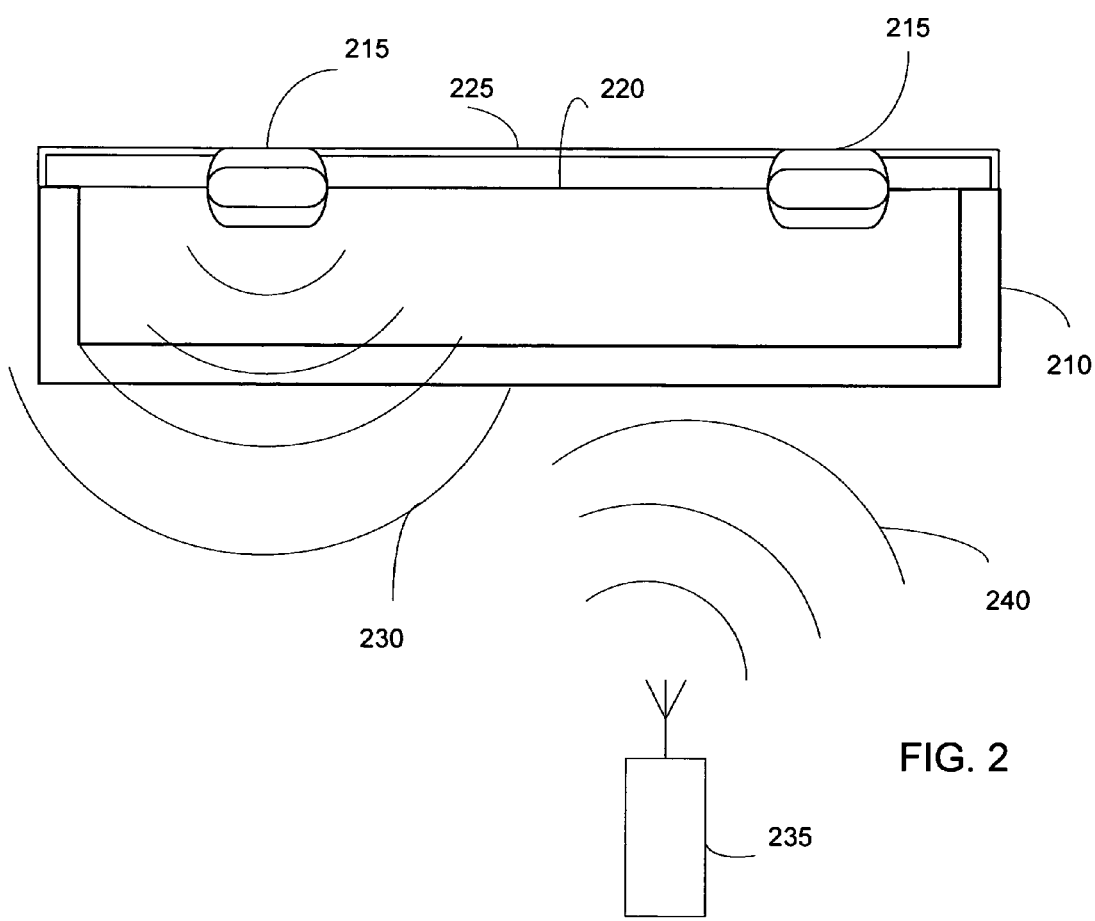
FIG. 2 is a schematic diagram of a smart instrument tray and a wireless reader according to an embodiment of the invention.

According to another feature of an embodiment of the invention, (FIG. 2), a plurality of smart instrument trays 210 may arrive at a distribution center, each of which optionally contains a plurality of RFID tagged instruments. As the smart instrument tray 210 is presented into a wireless radio frequency field 240 of a reader device 235 that constantly emits an RF signal, the transceivers 215 along with the antenna 220, collect data from the RFID tagged instruments and passes the data in a wireless fashion 230 to the wireless reader 235 to determine actions needed to be taken. The various actions that may be taken include refurbishing, discarding, or any other action deemed necessary of the instruments.

Figure 3:
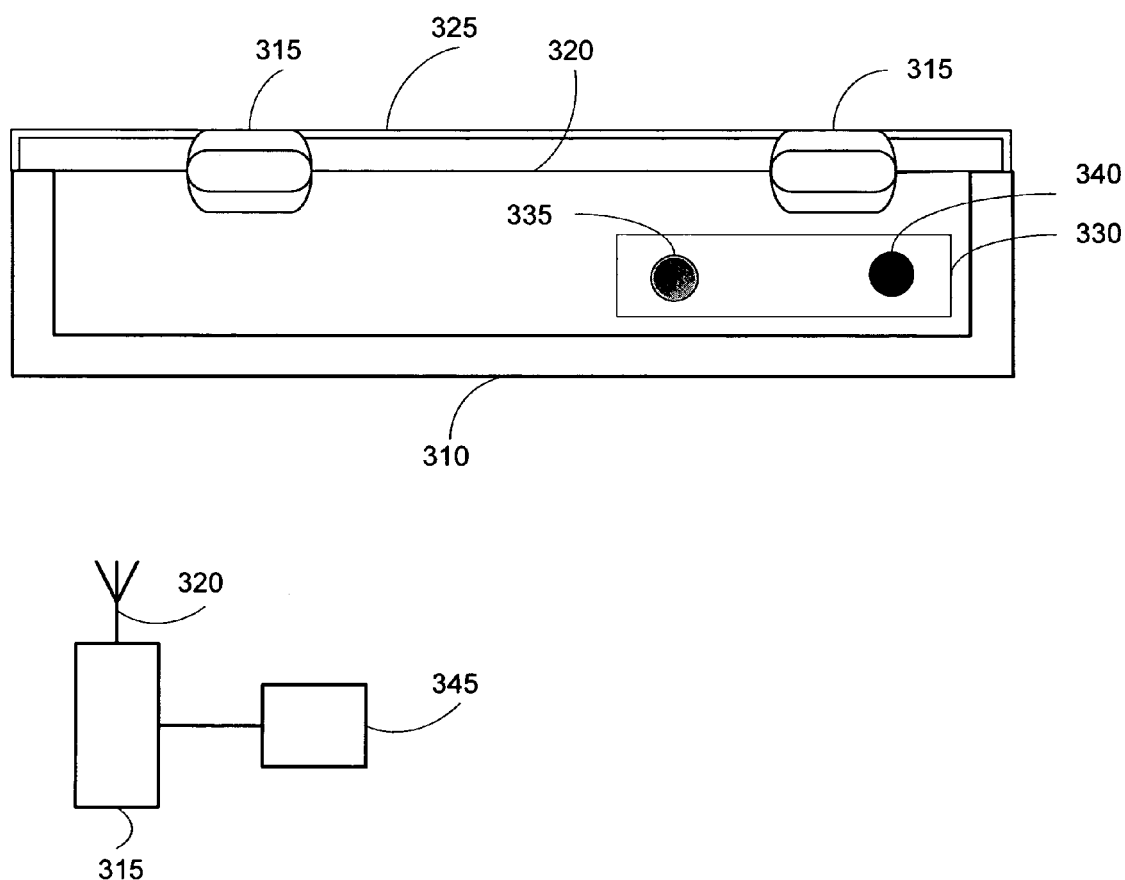
FIG. 3 is a schematic diagram of a smart instrument tray with a visual display according to an embodiment of the invention, along with a wireless reader with a database according to an embodiment of the invention.

Another feature of an embodiment of the present invention is shown with reference to FIG. 3. This preferred embodiment includes a method and apparatus for identifying and inventorying instruments used in surgical procedures. As shown in FIG. 3, there is a smart instrument tray 310, that optionally contains a plurality of RFID tagged medical and/or surgical instruments, wherein the RFID tags contain data identifying the instruments. In a preferred embodiment of the present invention, the RFID tags are interrogated by a combination of transceivers 315 and antenna 320, and in response to an interrogation signal, the RFID tags on the instruments respond by transmitting a signal back to the transceiver/antenna combination. The signal transmitted back preferably contains data, such as an individual identification number, manufacturer name, maintenance history of the instrument, and the like.

The data then can be compared against a database 345 containing information about the contents of each smart instrument tray. If it is determined that an individual RFID tag belongs to the individual instrument tray, a signal can be transmitted to module 330 on the exterior of the smart instrument tray 310, where a green light emitting diode 335 is activated. On the other hand, if data from an RFID tag does not match the information in the database 345, a signal can be transmitted to activate red LED 340 signifying that the instrument belongs to another instrument tray or some other inconsistency. This automatic signaling allows faster processing of inbound instrument trays that are returned from the customers. The LED signals may be replaced with any appropriate signaling system, apparatus, or device, including one that beeps or blinks or flashes.

Figure 4:
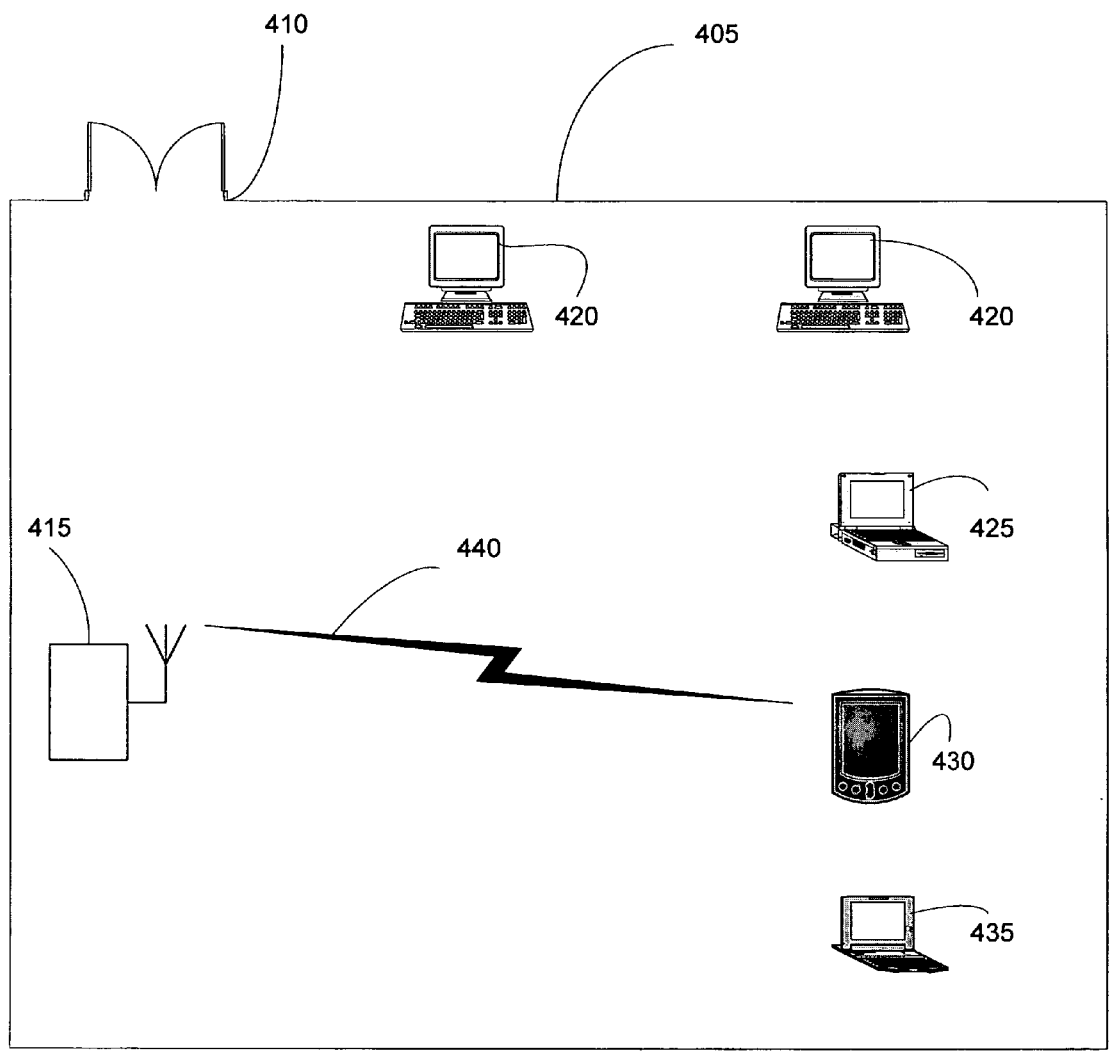
FIG. 4 is a schematic layout diagram of a distribution center illustrating a local wireless network according to an embodiment of the invention.

Another feature of an embodiment of the invention is illustrated with reference to FIG. 4. FIG. 4 illustrates a method and apparatus for identifying instruments and/or an instrument tray in a warehouse 405 where outbound instrument trays are packaged together, and where inbound instruments that arrive from customers are received and processed. In a typical embodiment, instrument tray 415, desktop personal computers 420, lap-top computer 425, personal digital assistant 430 (such as Palm™ Tungsten™), and optionally sub-notebook 435, make up a Wireless Fidelity local Area Network that implements a peer-to-peer network, that preferably implements IEEE 802.11 (b) standard, and employs a complementary code keying (CCK) modulation in order for the reader to distinguish the signal from others in the presence of substantial noise and multi-path interference. It is understood that not all of these items need be present to establish the network, and that various combinations/subcombinations of the items may be present in the network. The peer-to-peer network allows the wireless equipment in the warehouse to communicate with each other without the need for a gateway or an access point.

One aspect of this embodiment provides a method whereby: (i) a smart instrument tray 415, optionally containing a plurality of RFID tagged instruments, arrives at a central distribution center; (ii) a hand-held WiFi-capable personal digital assistant 430 transmits an interrogation signal 440; (iii) in response to the interrogation signal, a transceiver/antenna combination, which preferably is incorporated into the smart instrument tray 415 and/or plurality of RFID tagged instruments, interrogates the RFID tagged individual instruments and receives a data signal back; (iv) the transceiver/antenna combination transfers the data to the digital assistant 430; and (v) the data are compared to information pertaining to the history of each individual instrument.

Systems have been developed for identifying an object on a remote basis. Such systems include a reader displaced from the object for interrogating a tag at the object. The tag has an identifying code which is individual to the object being interrogated. This code typically is represented by a sequence of binary 1's and binary 0's in a pattern individual to the object, and in patterns to describe certain features of the individual object.

Referring again to FIG. 1, the RFID tag preferably includes a combined receiving and transmitting antenna 115, and a transceiver 110, which can contain one or more amplifiers, key means, sawtooth pulse generator, a frequency converter, and electronically programmable, integrated circuit memory. The integrated circuit memory may be a random access memory (RAM). The tag preferably is adapted to deliver stored information to a recording unit (indicated for example, at 430 in FIG. 4) upon instruction or request therefrom. The storing of information in the memory of the RFID tag can be accomplished in accordance with the procedures set forth in U.S. Pat. No. 4,390,880, the disclosure of which is incorporated by reference herein in its entirety.

For example, a signal 240 (FIG. 2) that is coded, preferably is emitted from the recording unit or reader 235 to the RFID tag transceiver 215 and received by the antenna 220. The signal 240 may include a key signal component, which typically is of such a nature that it corresponds to a preselected key code, and it actuates the key means that preferably is included in the transceiver 215, which, in turn, places the memory in condition for storing coded binary information contained in the signal 240 in the form of a pulse train.

More specifically, the signal 240 may be modulated onto an appropriate radio wave by an unshown modulator in the recording unit or reader device 235. The thusly modulated carrier wave is transmitted from the recording unit or reader device 235 for reception at antenna 220. Such modulation may be of any suitable type, such as amplitude modulation. For example, the amplitude modulation may be 100% such that the carrier or radio frequency signal is transmitted in pulse-representing bursts. It will be appreciated that any suitable mechanism may be employed for transmitting the signal 240.

The received, modulated carrier wave at antenna 220 preferably is fed to an envelope detector or the like (which may be a simple rectifying diode) where it is detected (demodulated) to recover or retrieve the modulating signal. The transmitted signal may be made up of two separate signals or signal components that are transmitted one after the other, one being the above-mentioned key signal component, and the other being the information bearing signal component. It is understood that even though the information bearing signal and the key signal are referred to as components of signal, they are not necessarily modulated onto the radio wave simultaneously, but instead can be transmitted one after another. The key signal component immediately precedes the information-bearing signal component in the signal. Each of the key and information-bearing signal components in the signal preferably is advantageously a binary coded digital signal in the form of a pulse train.

Following detection at the transceiver 215, the signal 240 is fed to an optional amplifier circuit that amplifies the signal. The optional amplifier circuit also preferably includes a decoding means for decoding the coded information in signal 240. The key means preferably is connected to the output of amplifier circuit to receive the key signal component in signal 240. The key means can compare the received key signal with a key code that is stored in the key means, and if the received key signal corresponds to the stored key code, the key means operates to feed a write signal to the memory via a conductor or the like. The write signal places the memory in its write mode and hence in a condition to store incoming data or information. The information-bearing signal or signal component of signal 240 then preferably is fed via a conductor or the like to the data input of the memory and is stored in memory if the received key signal component conforms to the stored key code to cause the generation of the write signal.

The key signal mentioned above preferably is of such a nature to keep reflections from an emitted signal or a signal emitted from an unknown transmitter from placing the memory in its write mode. In this manner, the operation of the key means with the key signal has the effect of avoiding or reducing the chance of storing undesired information in the memory. After storing the information, the key means removes the write signal from the memory so that the memory is rendered incapable of storing undesirable information. The pulse amplifier (if present), key means, and memory are of suitable known types, and any of the known types or later discovered types can be used in the present invention. The memory capacity in the memory may be, for example, 64 bits or higher. A voltage source, for example a battery with long service life, preferably powers the memory unit so that the information fed into the memory is retained. The data speed of the memory is designed to be sufficient to transfer code depending on the relative speed between the transceiver 215 and the recording unit or reader device 235. Those skilled in the art are capable of designing the data speed of the memory depending on the desired relative speeds, using the guidelines provided herein.

Read-out of information stored in the memory and transmission of the read-out information from the transceiver 215 to the reading device 235 preferably proceeds as follows. The reading device 235 is selectively operated to emit an interrogation signal 240 (a radio frequency wave) to the transceiver 215. This interrogation signal is received by the transceiver 215 to initiate transmission of the information stored in the memory. The information read out of the memory, typically in the form of a digital binary coded pulse signal then can be fed via a conductor to a generator. The generator preferably is controlled by the read-out signal on the conductor in such a manner that it emits a pulsating sawtoothed shaped signal, which corresponds to the pulse signal. The coded sawtooth signal emitted by the generator then preferably is impressed on a phase modulating diode in a frequency converter. As a result, the frequency converter emits to the antenna 220 a sideband that is provided with a code corresponding to the coded sawtooth shaped signal. The sideband signal is fed to antenna 220 from which it is re-emitted to the reading device 235. Upon reception of the coded sideband signal, the reading device 235 decodes it and processes it further to recover the transmitted information.

The information stored in the memory of the transceiver 215 may be an identification code that identifies and is individual to the particular instrument in which the transceiver is implemented or attached to. Thus, the sideband signal transmitted from the transceiver 215 in response to the reception of the interrogating signal 240 will contain the stored identification code. The identification code or other information that is stored in the memory is to be distinguished from the key code, which is stored in key means. As will be appreciated by those skilled in the art, the key code may be the same for a large number of transceivers (e.g., instrument trays and medial and/or surgical instruments) in the overall communication system because the purpose of the key means is to prevent the memory from being keyed (i.e., placed in its write mode) by spurious signals.

The antenna 220 preferably is a combined transmitting and receiving antenna of suitable, conventional construction. Advantageously, the radio wave containing the information and key signals is emitted from reading device 235 with a polarization that is orthogonal to the interrogating signal 240, which also is emitted by the reading device 235. From this description, it will be appreciated that the transceiver 215 preferably is equipped with two channels in which each respective signal is received.

A remote-programmable recording device according to preferred embodiments of the present invention render it possible to enter the information concerning, for example, identity, frequency of use, destination, etc. in transceivers 215 positioned on surgical trays and medical and/or surgical instruments, and at a later occasion to take out the information by an interrogation signal from a reading device 235.

The use of radio frequency signals with metallic objects such as stainless steel instrument trays and medical and surgical instruments can present certain problems. First, the metal used to fabricate the items may interfere with the transmission and reception of the radio frequency signals. Second, the antennae and transceivers present on the items need to be fabricated of materials capable of withstanding sterilization conditions, such as high pressures and temperatures. Therefore, it is preferred in the present invention to employ RFID tags encased in materials such as Phenol, Glass, Wood, Epoxy resin, Silicon, Rubber, Polyvinyl Chloride, commonly known as PVC, Acrylonitrile Butadiene Styrene, known as ABS resin, common plastics, Styrofoam, etc., but may include other suitable materials. It also is understood by skilled artisans that sufficient air-gap is required between the RFID tag, and the tagged instrument on one hand, and between the RFID tag and its encasement. Using the guidelines provided herein, those skilled in the art will be capable of designing a suitable RFID tag to be used on an instrument tray and/or a variety of surgical instruments.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. A method for obtaining information concerning the contents of an instrument tray, comprising:
   tagging one or more instruments positioned in or on an instrument tray with a radio frequency identification tag;
   positioning one or more antennas on the instrument tray;
   positioning a transceiver device on the instrument tray;
   presenting the instrument tray into a wireless radio frequency field of a reader device;
   receiving data from the radio frequency tagged instruments;
   transmitting an RF signal containing the data of the radio frequency tagged instruments by the transceiver; and
   comparing the radio frequency tagged instrument data to a database that resides in the reader device, wherein the RF signal emitted from an instrument is picked up by the internal antennas and routed to the wireless transceiver on the tray.

2. The method of claim 1, wherein the one or more antennas are positioned on the inside of the instrument tray and are activated by an RF field transmitted by the reader device.

3. The method of claim 1, wherein the one or more antennas are positioned on the inside of the instrument tray and emit an RF signal that activates the RF tags on each instrument in the tray.

4. The method of claim 1, wherein the reader device is one or more components selected from the group consisting of a desk computer, a hand-held computer, a personal digital assistant, and combinations thereof.

5. The method of claim 1, wherein tagging the one or more instruments comprises tagging the instruments with an RFID tag containing information selected from one or more of the group consisting of a part number, name, manufacturer, age, and the number of times the instrument has been sent to a client.

6. The method of claim 1, wherein transmitting the radio frequency signals comprises transmitting the radio frequency signals through proximity electromagnetic coupling.

7. The method of claim 1, wherein transmitting the radio frequency signals comprises transmitting the radio frequency signals through inductive coupling.

8. The method of claim 1, wherein transmitting the radio frequency signals comprises transmitting the radio frequency signals based upon propagating electromagnetic waves.

9. A method for obtaining information concerning the contents of an instrument tray, comprising:
   tagging one or more instruments positioned in or on one or more instrument trays with a radio frequency identification tag;
   positioning one or more antennas on the instrument tray;
   positioning a transceiver device on the instrument tray;
   providing a data output module on the instrument tray for displaying a signal;
   receiving data from the radio frequency identification tagged instruments;
   comparing the radio frequency tagged instrument data to a database to obtain information about the contents of the instrument tray; and
   activating the output module to output an output signal based on results of comparing.

10. The method of claim 9, wherein the data output module comprises light emitting diodes.

11. The method of claim 10, wherein a green light emitting diode is activated when the radio frequency tagged instrument data is consistent with the information in the database.

12. The method of claim 10, wherein a red light emitting diode is activated when the radio frequency tagged instrument data differs from the information in the database.

13. A method for obtaining information concerning the contents of an instrument tray, comprising:
   tagging one or more instruments positioned in or on an instrument tray with a radio frequency identification tag;
   enabling the instrument tray for a wireless fidelity local area network;
   positioning one or more antennas on the instrument tray;
   positioning a transceiver device on the instrument tray;
   presenting the instrument tray into a wireless radio frequency field of one or more wireless fidelity local area network enabled reader devices;
   receiving data from the radio frequency tagged instruments;
   transmitting an RF signal containing the data of the radio frequency tagged instruments by the transceiver device on the tray to the one or more wireless fidelity local area network enabled reader devices;
   comparing the radio frequency tagged instrument data to a database to obtain information about the contents of an instrument tray, and
   activating an output device on the instrument tray to output an output signal based on results of comparing.

14. The method of claim 13, wherein the one or more wireless fidelity local area network enabled reader devices is selected from one or more of the group consisting of a desk-top computer, a lap-top computer, a personal digital assistant, and a sub-notebook.

15. An apparatus for obtaining information concerning the contents of an instrument tray, comprising:
   at least one radio frequency identification tag for identifying instruments;
   one or more antennas positioned on an instrument tray;
   a reader device that wirelessly receives and transmits a radio frequency field that the instrument tray is presented to;

a transceiver device positioned on the instrument tray for receiving and transmitting radio frequency signals to and from the reader device;

a data decoder for comparing data from a radio frequency tagged instrument to a database to obtain information about the contents of the instrument tray; and a data output module on the instrument tray that is adapted to provide an output signal based on the comparison.

16. The apparatus of claim 15, wherein the at least one radio frequency identification tag comprises information selected from one or more of the group consisting of a part number, name, manufacturer, age, and the number of times the instrument has been sent to a client.

17. The apparatus of claim 15, wherein the transceiver device positioned on the instrument tray transmits radio frequency signals.

18. The apparatus of claim 15, wherein the one or more antennas positioned on the instrument tray receives the transceiver transmitted radio frequency signals.

19. The apparatus of claim 15, wherein radio frequency signals emitted from the instrument tray is transmitted via a wireless protocol to a transceiver in the form of a hand-held or field station reader.

20. The apparatus of claim 15, wherein the transceiver device transmits the radio frequency signals via proximity electromagnetic coupling.

21. The apparatus of claim 15, wherein the transceiver device transmits the radio frequency signals via inductive coupling.

22. The apparatus of claim 15, wherein the transceiver device transmits the radio frequency signals based upon propagating electromagnetic waves.

23. An apparatus for obtaining information concerning the contents of an instrument tray, comprising:

at least one radio frequency identification tag for identifying instruments;

one or more antennas positioned on an instrument tray;

a reader device that wirelessly receives and transmits a radio frequency field that the instrument tray is presented to;

a data output module positioned on the instrument tray for displaying a signal;

a transceiver device positioned on the instrument tray for receiving and transmitting radio frequency signals to and from the reader device; and a data decoder for comparing the radio frequency tagged instrument data to a database to obtain information about the contents of the instrument tray, wherein the data output module is adapted to output a signal indicative of results of comparing.

24. The apparatus of claim 23, wherein the data output module comprises light emitting diodes.

25. The apparatus of claim 24, wherein a green light emitting diode is activated when the radio frequency tagged instrument data is consistent with the information in the database.

26. The apparatus of claim 24, wherein a red light emitting diode is activated when the radio frequency tagged instrument data differs from the information in the database.

27. An apparatus for identifying the contents of an instrument tray, comprising:

at least one radio frequency identification tag for identifying instruments;

an instrument tray enabled for a wireless fidelity local area network;

one or more antennas positioned on the instrument tray;

one or more wireless fidelity local area network enabled reader devices that wirelessly receive and transmit a radio frequency field that the instrument tray is presented to;

a transceiver device positioned on the instrument tray for receiving and transmitting radio frequency signals to and from the reader device;

a data decoder for comparing data from a radio frequency tagged instrument to a database for obtaining information about the contents of the instrument tray; and a data output module positioned on the instrument tray adapted to output a signal based on the comparison.

28. The apparatus of claim 27, wherein the one or more wireless fidelity local area network enabled reader devices is selected from one or more of the group consisting of a desk-top computer, a lap-top computer, a personal digital assistant, and a sub-notebook.

* * * * *